(12) United States Patent
Brown et al.

(10) Patent No.: US 8,759,303 B2
(45) Date of Patent: Jun. 24, 2014

(54) COMPOSITIONS AND METHODS FOR TREATING MYELODYSPLASTIC SYNDROME

(75) Inventors: Gail L. Brown, Woodside, CA (US); Lixin Meng, Cupertino, CA (US)

(73) Assignee: Telik, Inc., Palo Alto, CA (US)

( * ) Notice: Subject to any disclaimer, the term of this patent is extended or adjusted under 35 U.S.C. 154(b) by 300 days.

(21) Appl. No.: 13/108,754

(22) Filed: May 16, 2011

(65) Prior Publication Data

US 2011/0301198 A1 Dec. 8, 2011

Related U.S. Application Data

(60) Provisional application No. 61/352,373, filed on Jun. 7, 2010.

(51) Int. Cl.
*A61K 38/05* (2006.01)
*A61K 31/40* (2006.01)
*A01N 43/38* (2006.01)

(52) U.S. Cl.
USPC ........................................ 514/21.91; 514/414

(58) Field of Classification Search
None
See application file for complete search history.

(56) References Cited

U.S. PATENT DOCUMENTS

| | | | |
|---|---|---|---|
| 5,763,570 | A | 6/1998 | Kauvar et al. |
| 5,955,432 | A | 9/1999 | Kauvar et al. |
| 5,965,164 | A | 10/1999 | Fuisz et al. |
| 7,029,695 | B2 | 4/2006 | Redelmeier et al. |
| 2009/0286752 | A1 | 11/2009 | Etter et al. |

FOREIGN PATENT DOCUMENTS

| | | |
|---|---|---|
| EP | 1880722 | 1/2008 |
| WO | WO-95/08563 | 3/1995 |
| WO | WO 2004035064 A1 | 4/2004 |
| WO | WO-2005/065639 | 7/2005 |
| WO | WO-2008/090569 | 7/2008 |
| WO | WO-2009/022355 | 2/2009 |
| WO | WO-2009/047799 | 4/2009 |

OTHER PUBLICATIONS

U.S. Appl. No. 13/108,752, filed May 2011, Brown.*
U.S. Appl. No. 13/108,756, filed May 2011, Brown et al.*
Anonymous, Telik initiates phase I trial of ezatiostat in patients with myelodysplastic syndrome, Thomson Reuters Drug News, Jan. 27, 2010.*
NCT01062152, version Apr. 28, 2010, available at http://clinicaltrials.gov/archive/NCT01062152/2010_04_28 on Jul. 25, 2013 ("NCT01062152").*
NCT00700206, version Jun. 6, 2009, available at http://clinicaltrials.gov/archive/NCT00700206/2009_06_06 on Jul. 25, 2013 ("NCT00700206").*
U.S. Appl. No. 13/041,136, filed Mar. 4, 2011, Parent et al.
U.S. Appl. No. 13/075,116, filed Mar. 29, 2011, Lum et al.
U.S. Appl. No. 13/094,693, filed Apr. 26, 2011, LeClerc et al.
U.S. Appl. No. 13/108,752, filed May 16, 2011, Brown.
U.S. Appl. No. 13/108,756, filed May 16, 2011, Brown et al.
U.S. Appl. No. 13/246,732, filed Sep. 27, 2011, Lum et al.
Author Unknown, "Telik initiates phase I trial of ezatiostat in patients with myelodysplastic syndrome", Thomson Reuters Integrity, 2010, Retrieved from the Internet: URL:https://integrity.thomson-pharma.com/integrity/xmlxsl/pk_ref_list.xml_show_ficha_ref?p_re_id=1444034.
Author Unknown, "Dose-Ranging Study of Telintra® Tablets + Revlimid® in Patients with Non-Deletion (5q) Low to Intermediate-1 Risk Myelodysplastic Syndrome (MDS)", Clinical Trials, 2010, Retrieved from the Internet: URL:http://clinicaltrials.gov/ct2/show/NCT01062152?term=ezatiostat&rank=2.
Author Unknown, "Phase 2 Study Comparing Two Dose Schedules of Telintra™ in Myelodysplastic Syndrome (MDS)", 2008, Retrieved from the Internet: URL:http://clinicaltrials.gov/ct2/show/NCT00700206?term=ezatiostat&rank=3.
Author Unknown, "Telik initiates Telintra Phase 2 trial in Revlimid refractory or resistant, del 5q MDS", 2011, Abstract, retrieved from Internet: URL:http://www.new-medical.net/new/20110608/Telik-initiates-Telintra-Phase-2-trial-in-Revlimid-refractory-or-resistant-del-5q-MDS.aspx.
Author Unknown, "Telik reports phase II data on ezatiostat in MDS", Thomson Reuters Integrity, 2010, Retrieved from the Internet: URL:https://integrity.thomson-pharma.com/integrity/xmlxsl/pk_ref_list.xml_show_ficha_ref?p_ref_id=1513842.
Lyttle et al. "Isozyme-specific Glutathione-S-Transferase Inhibitors: Design and Synthesis," Journal of Medicinal Chemistry, American Chemical Society, 1994, 37:189-194.
Quddus et al. "Oral Ezatiostat HCl (TLK199) and Myelodysplastic syndrome: A case report of sustained hematologic response following an abbreviated exposure", Journal of Hematology & Oncology, 2010, 3:16.
Raza et al. "Phase 1 multicenter dose-escalation study of ezatiostat hydrochloride (TLKI99 tablets), a novel glutathione analog prodrug, in patients with myelodysplastic syndrome", Blood, 2009, 113(26):6533-6540.
Raza et al. "Phase 2 Randomized Multicenter Study of Extended Dosing Schedules of Oral Ezatiostat HCl (Telintra), a Glutathione Analog Prodrug GSTP1-1 Inhibitor, In Low to Intermediate-1 Risk Myelodysplastic Syndrome (MDS)", Myelodysplastic Syndromes: Poster II, Abstract 2910, Blood, 2010, 116(21):1198.
Raza et al. "Phase 1 Dose Escalation Study of TLK199 Tablets (Telintra), a Novel Glutathione Analog, in Myelodysplastic Syndrome," Abstract #1454 appears in Blood, vol. 110, issue 11, Nov. 16, 2007.
Raza et al. "Phase 1-2a multicenter dose-escalation study of ezatiostat hydrochloride liposomes for injection (Telintra®, TLKI99), a novel glutathione analog prodrug in patients with myelodysplastic syndrome," Journal of Hematology & Oncology, 2009, 2:20.
Yoshioka et al . "Crystalline State and Polymorphism in Solid Drugs," In: "Stability of drugs and dosage forms," Kluwer Academic, 2000, ISBN: 0-306-46404-7, Chapter 2.2.11, pp. 107-108.

(Continued)

*Primary Examiner* — Svetlana M Ivanova
(74) *Attorney, Agent, or Firm* — Foley & Lardner LLP

(57) ABSTRACT

This invention generally relates to compositions and methods for treating myelodysplastic syndrome. In one embodiment, this invention relates to methods for treating myelodysplastic syndrome with ezatiostat or a salt thereof and lenalidomide.

7 Claims, No Drawings

(56) References Cited

OTHER PUBLICATIONS

Raza, et al. Phase 1 dose-ranging study of ezatiostat hydrochloride in combination with lenalidomide in patients with non-deletion (5q) low to intermediate-1 risk myelodysplastic syndrome (MDS). J Hematol Oncol. 2012; 5:18, pp. 1-8.

Gore, et al., "Future directions in Myelodysplastic Syndrome: Newer agents and the role of combination approaches", Cancer Control, vol. 15, No. 4 Supplement, pp. 40-49 (2008).

Neyns, et al. A multicenter cohort study of dose-dense temozolomide (21 of 28 days) for the treatment of recurrent anaplastic astrocytoma or oligoastrocytoma. Cancer Invest., 26(3):269-77 (2008).

Steensma, et al., "Novel therapies for Myelodysplastic syndromes", Hematology/Oncology Clinics of North America, vol. 24, Issue 2, pp. 423-441 (2010).

National Cancer Insitute (NCI) Sheet Myelodysplastic Syndromes Treatment, pp. 1-4 (2007).

Brown, Lyko F. DNA methyltransferase inhibitors and the development of epigenetic cancer therapies. J Natl Cancer Inst., 19;97(20):1498-506 (2005).

Office Communication for U.S. Appl. No. 13/108,752, filed May 16, 2011.

Office Communication for U.S. Appl. No. 13/108,756, filed May 16, 2011.

* cited by examiner

US 8,759,303 B2

COMPOSITIONS AND METHODS FOR TREATING MYELODYSPLASTIC SYNDROME

CROSS-REFERENCE TO RELATED APPLICATION

This application claims the benefit under 35 USC 119(e) of U.S. Provisional Application No. 61/352,373, filed Jun. 7, 2010, which is incorporated herein by reference in its entirety.

FIELD OF THE INVENTION

This invention relates to compositions and methods for treating myelodysplastic syndrome.

STATE OF THE ART

Myelodysplastic syndrome(s) (MDS) refers to a heterogeneous group of clonal hematopoietic stem cell disorders characterized by ineffective hematopoiesis (blood cell production) involving one or more cell lineages (red blood cells, white blood cells or platelets) and a variable risk of transformation to acute myeloid leukemia (AML). This syndrome becomes more common with age. It is estimated that MDS affects approximately 300,000 people worldwide. According to the American Cancer Society, 10,000 to 20,000 new cases of MDS are diagnosed each year in the United States alone. Survival rates using current therapy range from 6 months to 6 years with patients often requiring blood transfusions to manage their disease.

Currently, there are three approved drugs for treating MDS by the U.S. Food and Drug Administration (FDA). Lenalidomide is indicated for the treatment of transfusion dependent MDS patients with del(5q) and lower risk disease while azacytidine and decitabine are approved for all categories. With the exception of del(5q) patients, the response rate is approximately 50%, highlighting the need for clinical trials of new agents.

Ezatiostat and its salts are disclosed in U.S. Pat. No. 5,763,570. Ezatiostat has the IUPAC chemical name of ethyl (2S)-2-amino-5-[[(2R)-3-benzylsulfanyl-1-[[(1R)-2-ethoxy-2-oxo-1-phenylethyl]amino]-1-oxopropan-2-yl]amino]-5-oxopentanoate.

One example of a salt of ezatiostat is the hydrochloride salt, ezatiostat hydrochloride (USAN), which has the molecular weight of 566.1, the trademark of Telintra®, and the CAS registry number of 286942-97-0. U.S. patent application Ser. No. 13/041,136, filed Mar. 4, 2011, describes ansolvate and polymorphs of ezatiostat hydrochloride.

Ezatiostat hydrochloride has been evaluated for the treatment of MDS, in a Phase I-IIa study using a liposomal formulation (U.S. Pat. No. 7,029,695), as reported at the 2005 Annual Meeting of the American Society for Hematology (Abstract #2250) and by Raza et al. in *Journal of Hematology & Oncology*, 2:20 (published online on 13 May 2009); and in a Phase I study using a tablet formulation, as reported at the 2007 Annual Meeting of the American Society for Hematology (Abstract #1454) and by Raza et al. in *Blood*, 113:6533-6540 (prepublished online on 27 Apr. 2009), and in a single patient case report by Quddus et al. in *Journal of Hematology & Oncology*, 3:16 (published online on 23 Apr. 2010).

The entire disclosures of each of the patents, patent applications, and publications referred to in this application are incorporated into this application by reference.

SUMMARY OF THE INVENTION

In one embodiment, this invention is a method of treating MDS in a patient wherein the patient has prior exposure to lenalidomide which method comprises treating said patient with ezatiostat or a pharmaceutically acceptable salt thereof.

In one embodiment, this invention is a method of treating MDS by administration of ezatiostat or a salt thereof and lenalidomide.

In another embodiment, this invention is a method of treating MDS by administration of ezatiostat or a salt thereof and lenalidomide followed by administration of ezatiostat or a salt thereof alone.

In some embodiments, ezatiostat or a salt thereof is administered daily for at least 2 weeks. In some embodiments, ezatiostat or a salt thereof is administered daily for at least 3 weeks.

In the methods of this invention, ezatiostat or a salt thereof may be administered by a dosing regimen described in U.S. patent application Ser. No. 13/108,752, titled "COMPOSITIONS AND METHODS FOR TREATING MYELODYSPLASTIC SYNDROME," filed on May 16, 2011, which is incorporated by reference in its entirety and claims priority to U.S. Provisional Application No. 61/352,371, filed on Jun. 7, 2010. For example, ezatiostat or a salt thereof may be administered in cycles of 2 gram/day orally for 3 weeks on/1 week off, or cycles of 3 gram/day orally for 2 weeks on/1 week off. Equivalent ezatiostat doses for ezatiostat itself or other ezatiostat salts, or for other routes of administration may also be used.

In another aspect, this invention provides a composition comprising lenalidomide and ezatiostat or a salt thereof. Such compositions preferably contain a pharmaceutically acceptable excipient to facilitate administration.

In still another aspect, this invention provides a kit for the treatment of MDS comprising a first composition comprising lenalidomide and a second composition comprising ezatiostat or a salt thereof.

These and other embodiments of this invention are further described in the text that follows.

DETAILED DESCRIPTION OF THE INVENTION

Prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of pharmaceutically acceptable excipients.

1. Definitions

Unless defined otherwise, all technical and scientific terms used herein have the same meaning as commonly understood by one of ordinary skill in the art to which this invention belongs. As used herein the following terms have the following meanings.

The term "comprising" or "comprises" means that the compositions and methods include the recited elements, but do not exclude others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" means excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 15%, 10%, 5% or 1%.

"Lenalidomide" (Revlimid®, also known as Revamid in the UK) is an immunomodulatory agent with antiangiogenic and antineoplastic properties. It has the chemical name of 3-(4-amino-1-oxoisoindolin-2-yl)piperidine-2,6-dione or 1-oxo-2-(2,6-dioxopiperidin-3-yl)-4-aminoisoindoline or 3-(7-amino-3-oxo-1H-isoindol-2-yl)piperidine-2,6-dione, and CAS registry number of 191732-72-6. Lenalidomide is indicated for the treatment of patients who are transfusion-dependent due to low- or intermediate-1 risk MDS associated with a deletion 5q cytogenetic abnormality. Lenalidomide is available in 5 milligram (mg), 10 mg, 15 mg and 25 mg capsules for oral administration.

The term "therapeutically effective amount" refers to the amount of either lenalidomide or ezatiostat or a salt thereof, or the combination ("together"), that is an amount sufficient to effect treatment, as defined herein, when administered to a subject in need of such treatment. In one embodiment, the therapeutically effective amount will be up to 3.5 grams (g) of ezatiostat or a salt thereof administered per day. Preferably, ezatiostat or a salt thereof is administered in an amount of 2 grams per day and, more preferably, is administered twice a day in equal 1 gram doses. Such a therapeutically effective amount is particularly relevant when the treatment regimen is for 3 weeks of administration of ezatiostat or a salt thereof followed by a week of no administration of the drug. In another embodiment, the therapeutically effective amount will be 3 grams of ezatiostat or a salt thereof administered in a single dose, or in 2 equal daily doses of 1.5 grams. Such a therapeutically effective amount is particularly relevant when the treatment regimen is for 2 weeks of administration of ezatiostat or a salt thereof followed by a week of no administration of the drug. Preferably, the dosing regimen employs 2 grams of ezatiostat or a salt thereof administered in an amount of 1 gram doses twice a day either under continuous administration or with administration for 3 weeks followed by a week of no administration of the drug.

In one embodiment, the therapeutically effective amount will provide efficacious results in at least about 10% of the treated population, and preferably at least about 15%.

As used herein, the term "treatment" or "treating" means any treatment of MDS in a patient which produces one or more of the following:
  inhibiting the MDS, that is, arresting or suppressing the development of clinical symptoms (e.g., need for blood transfusion, abnormal blood count, and the like); and/or
  relieving the MDS, that is, causing the regression of symptoms.

As used herein, the term "patient" refers to mammals and includes humans and non-human mammals.

2. Methods

In one of its method aspects, this invention is directed to a method for treating a myelodysplastic syndrome (MDS) in a patient in need thereof wherein the patient has prior exposure to lenalidomide which method comprises treating said patient with ezatiostat or a pharmaceutically acceptable salt thereof.

It has been unexpectedly discovered that patients who were treated with lenalidomide prior to the treatment with ezatiostat hydrochloride exhibited higher response rate and/or duration as compared with patients who were not pre-treated with lenalidomide. For example, as shown in Table 2, the response rate in patients who were not pre-treated with lenalidomide is about 22% and in patients who were pre-treated with lenalidomide the response rate is about 46%, an over 100% increase in response rate.

The prior exposure to lenalidomide may be an administration of lenalidomide to the patient any time prior to administration of ezatiostat or a salt thereof. A typical lenalidomide treatment schedule involves a 28-day-cycle, during which lenalidomide is administered once a day, every day, for 21 days (3 weeks) followed by an interruption of 7 days (1 week) when no lenalidomide is administered. This 28-day-cycle can be repeated for a duration of up to 6 months. Lenalidomide capsules have four different strengths: 5 mg, 10 mg, 15 mg, and 25 mg.

In some embodiments of this invention, the patient has been treated with at least one dosage of lenalidomide. In some embodiments, the patient has been treated with lenalidomide for at least 2 days, 3 days, 4 days, 5 days, or 6 days. In some embodiments, the patient has been treated with lenalidomide for at least one week, two weeks or three weeks. In some embodiments, the patient has completed 1, 2, 3, 4, 5, or 6 lenalidomide treatment cycles. In some embodiments, the patient has completed the entire 6-month lenalidomide treatment regimen.

In some embodiments of this invention, the patient being treated with lenalidomide prior to administration of ezatiostat or a salt thereof has developed intolerance to lenalidomide and stopped treatment with lenalidomide or switched to a lower lenalidomide dosage before administration of ezatiostat or a salt thereof starts. It is to be understood that a patient may stop using lenalidomide or switch to a lower lenalidomide dosage after finishing a cycle or during the cycle depending on the patient's tolerance to lenalidomide.

As a derivative of thalidomide, lenalidomide may cause many side effects, such as birth defects and other adverse events. The reported adverse events include but are not limited to those related to:
  blood and lymphatic system disorders, such as thrombocytopenia, neutropenia, e.g., febrile neutropenia, leukopenia, anemia, hemolytic anemia, e.g., warm type hemolytic anemia, splenic infarction, bone marrow depression, coagulopathy, hemolysis, and refractory anemia;
  skin and subcutaneous tissue disorders such as rash, dry skin, contusion, night sweats, increased sweating, ecchymosis, and erythema;
  gastrointestinal disorders, such as diarrhea, constipation, nausea, abdominal pain, vomiting, abdominal pain upper, dry mouth, loose stools, gastrointestinal hemorrhage, colitis ischemic, intestinal perforation, rectal hemorrhage, colonic polyp, diverticulitis, dysphagia, gastritis, gastroenteritis, gastroesophageal reflux disease, obstructive inguinal hernia, irritable bowel syndrome, melena, pancreatitis due to biliary obstruction, pancreatitis, perirectal abscess, small intestinal obstruction, and upper gastrointestinal hemorrhage;
  respiratory, thoracic and mediastinal disorders such as nasopharyngitis, cough, dyspnea, pharyngitis, epistaxis, dyspnea exertional, rhinitis, and bronchitis;

musculoskeletal and connective tissue disorders such as arthralgia, back pain, muscle cramp, pain in limb, myalgia and peripheral swelling, arthritis, arthritis aggravated, gouty arthritis, neck pain, and chondrocalcinosis pyrophosphate;

benign or malignant neoplasms such as acute leukemia, acute myeloid leukemia, bronchoalveolar carcionoma, lung cancer, lymphoma, and prostate cancer;

nervous system disorders, such as dizziness, headache, hypoesthesia, dysgeusia, and peripheral neuropathy;

infections and infestations, such as pneumonia, urinary tract infection, sinusitis, cellulitis, infection, bacteremia, central line infection, clostridial infection, ear infection, *Enterobacter sepsis*, fungal infection, herpes viral infection, influenza, kidney infection, *Klebsiella sepsis*, lobar pneumonia, localized infection, oral infection, pseudomonas infection, septic shock, sinusitis acute, sinusitis, Staphylococcal infection, and urosepsis;

metabolism and nutrition disorders, such as hypokalemia, anorexia, hypomagnesemia, dehydration, gout, hypernatremia, and hypoglycemia;

psychiatric disorders such as insomnia, confusional state and depression;

renal and urinary disorders, such as dysuria, renal failure, hematuria, renal failure acute, azotemia, calculus ureteric, and renal mass;

reproductive system and breast disorders such as pelvic pain;

vascular and cardiac disorders such as hypertension, palpitations, cardiac failure congestive, atrial fibrillation, angina pectoris, cardiac arrest, cardiac failure, cardiorespiratory arrest, cardiomyopathy, myocardial infarction, myocardial ischemia, atrial fibrillation aggravated, bradycardia, cardiogenic shock, pulmonary edema, supraventricular arrhythmia, tachyarrhythmia, and ventricular dysfunction;

endocrine disorders such as acquired hypothyroidism;

ear and labyrinth disorders such as vertigo;

hepatobiliary disorders such as hyperbilirubinemia, cholecystitis acute, cholecystitis, and hepatic failure;

endocrine disorders such as Basedow's disease;

immune system disorders such as hypersensitivity;

general disorders, such as disease progression, fall, gait abnormal, intermittent pyrexia, nodule, rigors, and sudden death;

administrative site conditions, such as femur fracture, transfusion reaction, cervical vertebral fracture, femoral neck fracture, fractured pelvis, hip fracture, overdose, post procedural hemorrhage, rib fracture, road traffic accident, and spinal compression fracture; and other observations such as increased blood creatinine, decreased hemoglobin, liver function tests abnormal, increase in alanine aminotransferase, and increased troponin I.

Most common and/or severe adverse events include neutropenia, thrombocytopenia, pneumonia, rash, anemia, leukopenia, fatigue, dyspnea, back pain, febrile neutropenia, nausea, diarrhea, pyrexia, sepsis, dizziness, granulocytopenia, chest pain, pulmonary embolism, respiratory distress, pruritus, pancytopenia, muscle cramp, respiratory tract infection, upper respiratory tract infection, asthenia, multi-organ failure, epistaxis, hypoxia, pleural effusion, pneumonitis, pulmonary hypertension, vomiting, increased sweating, arthralgia, pain in limb, headache, and syncope.

In certain patient populations, one or more of the adverse events are so severe that lenalidomide can no longer be administered to the patient or lenalidomide must be administered in a reduced dosage. Under such circumstances, switching from lenalidomide to ezatiostat or a salt thereof or addition of ezatiostat or a salt thereof not only avoids the adverse effect, but may also provide better therapeutic effect for ezatiostat or a salt thereof.

In some embodiments of this invention, the patient being treated with lenalidomide prior to administration of ezatiostat or a salt thereof does not respond to lenalidomide or the response to lenalidomide does not continue with continued lenalidomide treatment. It is reported that about 50% of the patient administered lenalidomide exhibit clinically recognizable response. Under such circumstances, treating patients who did not respond or stopped responding to lenalidomide with ezatiostat hydrochloride results in an unexpected better therapeutic effect and reduction of clinical symptoms. In this case, treatment with lenalidomide may continue with administration of ezatiostat or a salt thereof at the same dosage or at a reduced dosage, or treatment with lenalidomide may be completely stopped.

In some embodiments, ezatiostat or a pharmaceutically acceptable salt thereof is administered daily for at least two weeks. In some embodiments, ezatiostat or a pharmaceutically acceptable salt thereof is administered daily for at least three weeks.

In another of its method aspects, this invention provides a method treating a myelodysplastic syndrome (MDS) in a patient, which method comprises concurrently administering to said patient lenalidomide and ezatiostat or a pharmaceutically acceptable salt thereof. In some embodiments, ezatiostat or a pharmaceutically acceptable salt thereof is administered daily for at least two weeks. In some embodiments, ezatiostat or a pharmaceutically acceptable salt thereof is administered daily for at least three weeks. In these cases, the patient may or may not have been treated with lenalidomide prior to administration of ezatiostat hydrochloride. The former includes situations described above.

When administered concurrently, lenalidomide and ezatiostat or a salt thereof can be administered in any manner in which the pharmacological effects of both are manifested in the patient at the same time. Thus, concurrent administration of lenalidomide and ezatiostat or a pharmaceutically acceptable salt thereof does not require that a single pharmaceutical composition, the same dosage form, the same route of administration be used for the two agents, the two agents be administered at the same time or the two agents be administered for a similar length of time. When administered by the same dosage form and the same route of administration, at substantially the same time, it could proceed by delivering both active ingredients simultaneously in a single novel pharmaceutical composition in accordance with the present invention. It is understood that in addition to the above, this invention contemplates that a concurrent administration may be the administration of a first and second pharmaceutical composition comprising lenalidomide and ezatiostat or a pharmaceutically acceptable salt thereof, respectively. The term "concurrent" includes both simultaneous delivery as well as sequential delivery wherein each drug is administered separately in a manner that provides serum levels of both drugs in the patient at the same time.

As noted above, a clinician employing lenalidomide alone in a patient for treating MDS may, at a point in that treatment regimen, add ezatiostat or a pharmaceutically acceptable salt thereof as an additional component for treating that patient. Such later addition of ezatiostat or a pharmaceutically acceptable salt thereof in combination with lenalidomide constitutes concurrent administration for the purposes of this invention as the effects of both will be manifested in the patient at the same time.

In another embodiment, this invention is a method of treating MDS by administration of ezatiostat or a salt thereof and lenalidomide followed by administration of ezatiostat or a salt thereof alone.

In some embodiments of this invention, when administered concurrently with ezatiostat or a pharmaceutically acceptable salt thereof, lenalidomide is administered in the typical 28-day-cycle as described above and may be given in any of the dosage strengths. In some embodiments, lenalidomide is administered at a reduced dosage and/or frequency, for example, lenalidomide may be administered once every other days, once every 3, 4, 5, or 6 days. Or it may be administered once a week or may be discontinued while treatment with ezatiostat or a pharmaceutically acceptable salt thereof continues.

Typically, ezatiostat or a salt thereof is administered in a therapeutically effective amount. In some embodiments, ezatiostat or a salt thereof is administered by a dosing regimen described in U.S. patent application Ser. No. 13/108,752, titled "COMPOSITIONS AND METHODS FOR TREATING MYELODYSPLASTIC SYNDROME," filed on May 16, 2011, which is incorporated by reference in its entirety.

In some embodiments, ezatiostat or a salt thereof is administered up to about 3.5 grams per day of ezatiostat hydrochloride, or an equivalent amount (in terms of ezatiostat content) of ezatiostat itself or another salt of ezatiostat. In a preferred embodiment, the dosing of ezatiostat or a salt thereof is a therapeutically effective amount of up to about 1.5 gram administered twice a day (b.i.d.).

In an embodiment of this invention, ezatiostat or a salt thereof is administered in 1 gram dosages twice a day for three weeks followed by an interruption of one week where ezatiostat or a salt thereof is not administered. After the interruption, the regimen can be repeated as necessary. This regimen may be referred to as the "three-week regimen."

In an embodiment of this invention, ezatiostat or a salt thereof is administered in 1.5 gram dosages twice a day for two weeks followed by an interruption of one week where ezatiostat or a salt thereof is not administered. After the interruption, the regimen can be repeated as necessary. This regimen may be referred to as the "two-week regimen."

In another embodiment of this invention, the patient is treated continuously with a therapeutically effective amount of ezatiostat or a salt thereof of up to 3 grams per day preferably administered in up to 1.5 gram dosages twice a day. In this embodiment, ezatiostat or a salt thereof can be administered so long as the patient is in need of and can tolerate such treatment. It is contemplated that in this embodiment, the therapeutically effective amount of ezatiostat or a salt thereof may be less or more than that when there is an interruption in the treatment regimen. This regimen may be referred to as the "continuous regimen."

While twice a day administration is preferred, it is contemplated that once a day administration or 3 times a day administration could be employed. In the former case, once a day administration would assist in patient compliance; whereas in the latter case, smaller tablets could be used for those patients who have difficulty swallowing larger tablets. The amount of drug administered would be adjusted so that the total drug administered per day is a therapeutically effective amount.

The treatment with ezatiostat or a salt thereof may involve one or a combination of two or more of the dosing regimens described herein. The following are exemplifying dosing schedules of ezatiostat hydrochloride:

1.5 gram ezatiostat hydrochloride administered twice per day for 2 weeks for an aggregate total dosing of 42 grams followed by a week when no ezatiostat or a salt is administered;

1 gram ezatiostat hydrochloride administered twice per day for 3 weeks for an aggregate total dosing of 42 grams followed by a week when no ezatiostat or a salt is administered;

1 gram ezatiostat hydrochloride administered twice per day continuously until the attending clinician deems it appropriate for the patient to be withdrawn from administration;

a therapeutically effective amount of up to 3 grams of ezatiostat hydrochloride per day administered in one, two, or three divided doses for 2 weeks followed by a week when no ezatiostat or a salt is administered;

a therapeutically effective amount of up to 2 grams of ezatiostat hydrochloride per day administered in one, two, or three divided doses for 3 weeks followed by a week when no ezatiostat or a salt is administered; and/or a therapeutically effective amount of up to 2 grams of ezatiostat hydrochloride per day administered in one, two, or three divided doses continuously until the attending clinician deems it appropriate for the patient to be withdrawn from administration.

Ezatiostat hydrochloride in the above dosings can be replaced with an equivalent amount of ezatiostat itself or another salt of ezatiostat (in terms of ezatiostat content).

When administration of ezatiostat or a salt thereof is twice a day, it is preferred that the interval between the first and second doses be from about 6 to 14 hours and preferably between about 8 and 14 hours.

In one embodiment, ezatiostat or a salt thereof, e.g., ezatiostat hydrochloride, can be administered intravenously as a lipid formulation such as those described in U.S. Pat. No. 7,029,695 which is incorporated by reference in its entirety.

In another embodiment, ezatiostat or a salt thereof, e.g., ezatiostat hydrochloride, can be administered orally. In one embodiment, ezatiostat or a salt thereof, e.g., ezatiostat hydrochloride, can be administered as a tablet formulation. Such a tablet formulation is disclosed in U.S. patent application Ser. No. 13/075,116, filed Mar. 29, 2011, titled "TABLET FORMULATION OF EZATIOSTAT," which is incorporated by reference in its entirety.

3. Composition

In another aspect, this invention provides a composition comprising lenalidomide and ezatiostat or a pharmaceutically acceptable salt thereof.

In some embodiments, the ezatiostat or the salt thereof and the lenalidomide together are in a therapeutically effective amount.

In some embodiments, lenalidomide and/or ezatiostat or a salt thereof is in a therapeutically effective amount. In some embodiments, the composition comprises about 5 mg, 10 mg, 15 mg or 25 mg of lenalidomide and about 200 mg, 300 mg, 400 mg, 500 mg, 600 mg, 700 mg, 800 mg, 900 mg, or 1000 mg ezatiostat or a salt thereof.

In one embodiment, lenalidomide may be added to the ezatiostat or a salt thereof lipid formulation described in U.S. Pat. No. 7,029,695.

In another embodiment, lenalidomide may be added to a ezatiostat or a salt thereof tablet formulation. Such a tablet formulation is disclosed in U.S. patent application Ser. No. 13/075,116, filed Mar. 29, 2011, titled "TABLET FORMULATION OF EZATIOSTAT," which is incorporated by reference in its entirety.

4. Kit

In still another aspect, this invention provides a kit for the treatment of MDS comprising a first composition comprising lenalidomide and a second composition comprising ezatiostat or a salt thereof, including those described herein.

In some embodiments, the ezatiostat or the salt thereof and the lenalidomide together are in a therapeutically effective amount.

In some embodiments, the kit further comprises a label with instructions to administer the first dose of lenalidomide 1 day, 2 days, 3 days, 4 days, 5 days, 6 days before the first administration of ezatiostat or a salt thereof. In some embodiments, the kit further comprises a label with instructions to administer lenalidomide 1 week, 2 weeks, 3 weeks, 4 weeks, 5 weeks, or 6 weeks before administration of ezatiostat or a salt thereof. In some embodiments, the kit further comprises a label with instructions to administer lenalidomide concurrently with ezatiostat or a salt thereof. In some embodiments, the kit further comprises a label with instructions to administer lenalidomide and ezatiostat or a salt thereof according to any of the dosing schedules described herein.

EXAMPLES

The present invention is further defined by reference to the following examples. It will be apparent to those skilled in the art that many modifications, both to materials and methods, may be practiced without departing from the scope of the current invention.

Ezatiostat Hydrochloride Tablets in Patients with an International Prognostic System Score (IPSS) Low to Intermediate-1 Risk Myelodysplastic Syndrome Eighty-seven patients were randomized and treated at 23 investigational sites. After initial dose ranging in 14 patients, two dose levels were selected for further study. Subsequently, 37 patients were treated at 3 grams daily for two weeks followed by a one week rest period, and 36 patients were treated at 2 grams daily for three weeks followed by a one week rest period. The data on these 73 patients was pooled for this preliminary analysis.

The median age was 72 years, with a patient population distribution of IPSS low risk (23 patients, 32%) and intermediate-1 risk (50 patients, 68%). Patients had received a median of three prior MDS therapies including, 34 patients (47%) with prior Revlimid® (lenalidomide) and 28 patients (38%) with prior DNA methyltransferase inhibitors (DMTI) [azacitidine, decitabine].

At the time of preliminary analysis, 8 patients remained on treatment for continuing clinical benefit. The overall Hematologic Improvement-Erythroid (HI-E) rate was 22%, 13 of 60 evaluable patients (95% CI, 12.1-34.2). The median duration of HI-E response was 46 weeks (range 2-51). The median hemoglobin level increased by 2.0 gram/dL in responders. Eleven of 38 red blood cell (RBC) transfusion-dependent patients (29%) had clinically significant RBC transfusion reductions (reduction of 4 U/8 weeks, IWG 2006) with 4 patients (11%) achieving RBC transfusion independence and 3 patients continuing on treatment. One patient continued in complete remission for more than 12 months following discontinuation of therapy (Quddus et. al., J. Hem. and Onc. April 2010, 3:15).

Telintra® continues to demonstrate multilineage hematologic improvement. There was a 15% Hematologic Improvement-Neutrophil (HI-N) rate observed in 3 of 20 patients (95% CI, 3.2-37.9), and the bilineage HI rate (HI-E and HI-N) was 11%, 2 of 19 patients (95% CI, 1.3-33.1).

There were three cytogenetic complete responses, one in a patient with 45X, −Y[4], 46, XY [16] abnormal cytogenetics that converted to normal after four cycles of therapy. Of the four patients enrolled in the study with del 5q minus, two had a complete cytogenetic response, including one who had failed prior Revlimid® therapy.

A planned logistic regression analysis was used to evaluate all known prognostic characteristics in order to define those patients who had an increased likelihood of HI-E response to Telintra®. Prior DMTI treatment predicts a five-fold decrease in the odds for a HI-E response to Telintra® (p=0.023). Prior Revlimid® treatment was observed to enhance HI-E response to Telintra®.

There was a 40% HI-E rate (6 of 15 patients, 95% CI, 16.3%-67.7%) in patients who had prior Revlimid® treatment, but no prior DMTI treatment. Within this patient group, five of 11 patients (45%) achieved significant RBC transfusion reduction with three of those patients (27%) achieving transfusion independence.

There was a 26% HI-E rate (6 of 23 patients, 95% CI, 10.2%-48.4%) in patients who had no prior Revlimid® treatment and no prior DMTI treatment. Within this group, five of 11 patients (45%) achieved significant RBC transfusion reduction.

There was a 0% HI-E rate (0 of 17 patients, 95% CI, 0%-19.5%) in patients who had no prior Revlimid® treatment but who had received prior DMTI treatment.

More than 403 cycles of Telintra® therapy have been administered. The safety data is based on all patients treated. The most common non-hematologic adverse events (AEs) were Grade 1 and 2 gastrointestinal (GI) respectively, nausea (45%, 16%), diarrhea (25%, 7%) and vomiting (30%, 12%). Grade 3 events were uncommon: nausea (1%), diarrhea (3%) and vomiting (2%). Prior DMTI treatment was associated with an increased incidence of GI AEs.

Telintra® treatment may result in clinically significant hematologic improvement in patients with MDS and may offer an alternative to RBC transfusions. These results are consistent with levels of efficacy observed in prior studies with Telintra®, the first GST P1-1 enzyme inhibitor tested in MDS patients.

Tables 1 and 2 summarize the results of this clinical study. As shown in Table 2, response rate to Telintra® increased from about 22.2% for patients who had no prior treatment with Revlimid® to about 46.2% in patients who had treatment with Revlimid® prior to administration of Telintra®.

TABLE 1

Hematological Improvement - Erythroid (HI-E): Time to
Response and Duration of Response Starting Telintra ®
Dose of 3,000 mg/day (1.5 g b.i.d.) or 2,000 mg/day (1 g b.i.d.)
(Efficacy Evaluable Population)

| | Telintra ® Dosing Schedule | |
|---|---|---|
| | 1.5 g b.i.d. 2 weeks on & 1 week off (N = 29) | 1 g b.i.d. 3 weeks on & 1 week off (N = 31) |
| Time to HI-E Response (Weeks) [1] | | |
| N | 7 | 6 |
| Mean | 8.4 (0.72) | 8.9 (1.29) |
| Median | 8.1 | 8.4 |
| Min, Max | 8.0, 10.0 | 8.0, 11.3 |
| Duration of HI-E Response (Weeks) [2] | | |
| # Event | 5 (71.4%) | 2 (33.3%) |
| # Censored | 2 (28.6%) | 4 (66.7%) |
| Median (95% CI) | 18.4 (3.1-51.0) | 46.1 (10.0-46.1) |
| Min, Max | 1.9-51.0 | 2.4-46.1 |

[1] Days from date of first dose of study medication to the date of first documentation of response plus one divided by 7.
[2] Total number of days of where response is seen divided by 7.

TABLE 2

Hematological Improvement - Erythroid (HI-E)
(Efficacy evaluable population)

| | | HI-E [3] Statistics | |
|---|---|---|---|
| Revlimid ® | N | Response (n) | Response Rate (95% Confidence Interval) |
| Yes | 13 | 6 | 46.2% (19.2%-74.9%) |
| No | 27 | 6 | 22.2% (8.6%-42.3%) |

[3] RBC transfusion reduction from baseline =>4 units per eight weeks; or patient with symptomatic anemia not transfusion dependent with hemoglobin <11 g/dL prior to treatment, achieving a hemoglobin increase by >=1.5 g/dL sustained for a period of eight weeks.

What is claimed is:

1. A method for treating a myelodysplastic syndrome in a patient, which method comprises concurrently administering to the patient ezatiostat or a salt thereof and lenatidomide, wherein the ezatiostat or the salt thereof and the lenalidomide are administered together in a therapeutically effective amount.

2. A method for treating a myelodysplastic syndrome in a patient, which method comprises concurrently administering to the patient ezatiostat or a salt thereof and lenatidomide, wherein the ezatiostat or the salt thereof and the lenalidomide are administered together in a therapeutically effective amount, and wherein the ezatiostat or the salt thereof is administered orally.

3. The method of claim 2, wherein the ezatiostat or the salt thereof is administered according to a treatment schedule comprising administration of a daily dosage of the ezatiostat or the salt thereof in an amount having ezatiostat that is equal to the ezatiostat in 2 grams of ezatiostat hydrochloride, which daily dosage is administered for three weeks followed by a one-week interruption wherein no ezatiostat or the salt thereof is administered.

4. The method of claim 2, wherein the ezatiostat or the salt thereof is administered according to a treatment schedule comprising administration of a daily dosage of the ezatiostat or the salt thereof in an amount having ezatiostat that is equal to the ezatiostat in 3 grams of ezatiostat hydrochloride, which daily dosage is administered for two weeks followed by a one-week interruption wherein no ezatiostat or the salt thereof is administered.

5. The method of claim 1, wherein the salt of ezatiostat is ezatiostat hydrochloride.

6. The method of claim 5, wherein the ezatiostat hydrochloride is administered according to a treatment schedule comprising administration of a daily dosage of 2 grams of ezatiostat hydrochloride for three weeks followed by a one-week interruption wherein no ezatiostat or a salt thereof is administered.

7. The method of claim 5, wherein the ezatiostat hydrochloride is administered according to a treatment schedule comprising administration of a daily dosage of 3 grams of ezatiostat hydrochloride for two weeks followed by a one-week interruption wherein no ezatiostat or a salt thereof is administered.

* * * * *